United States Patent
Mayer et al.

(10) Patent No.: US 7,488,840 B2
(45) Date of Patent: Feb. 10, 2009

(54) METHOD FOR PRODUCING 2-CHLOROMETHYLPHENYL ACETIC ACID DERIVATIVES

(75) Inventors: Guido Mayer, Gönnheim (DE); Oliver Cullmann, Heppenheim (DE); Bernd Wolf, Fußgönheim (DE); Michael Keil, Freinsheim (DE); Wassilios Grammenos, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 323 days.

(21) Appl. No.: 10/505,475

(22) PCT Filed: Feb. 6, 2003

(86) PCT No.: PCT/EP03/01160

§ 371 (c)(1),
(2), (4) Date: Aug. 24, 2004

(87) PCT Pub. No.: WO03/072538

PCT Pub. Date: Sep. 4, 2003

(65) Prior Publication Data

US 2005/0113597 A1    May 26, 2005

(30) Foreign Application Priority Data

Feb. 26, 2002  (DE) ............... 102 08 029

(51) Int. Cl.
C07C 229/00    (2006.01)
C07C 241/00    (2006.01)
(52) U.S. Cl. ........................ 560/35; 564/147
(58) Field of Classification Search ............... 560/35; 564/147
See application file for complete search history.

(56) References Cited

U.S. PATENT DOCUMENTS 6,114,342 A    9/2000  Oberdorf et al.

FOREIGN PATENT DOCUMENTS

WO    WO 97 21686 A    6/1997

OTHER PUBLICATIONS

Moody et al, Indium As a Reducing Agent: Deprotection of 4-Nitrobenzyl Ethers and Esters, Synlett 1999, No. 10, p. 1575-1576.*
Jempty et al., "Iron trichloride/silicon dioxide reacts as oxidant or Lewis aci with phenol ethers", Journal of Organic Chemistry (1981) 46(22), 4545-51.
Frost et al., "Indium triflate: An Efficient Catalyst for the Friedel-Crafts Acylation of Aromatics", Fourth International Electronic Conference on Synthetic Organic Chemistry, Sep. 1-30, 2000.
Vankar et al., "Selective Cleavage of Benzyl Ethers using the Boron Trifluoride-Ether and Sodium Iodide Reagent Systems", J. Chem. Research (S), 1985, 232-233.

* cited by examiner

*Primary Examiner*—Taylor Victor Oh
(74) *Attorney, Agent, or Firm*—Rothwell, Figg, Ernst & Manbeck

(57) ABSTRACT

The invention relates to a method for producing 2-chloromethylphenyl acetic acid derivatives of formula (I), in which X represents $C_1$-$C_4$ alkoxy or methylamino, by cleaving the ether bonds in compounds of formula (II), in which R represents $C_1$-$C_4$ alkyl, $C_1$-$C_4$ alkoxy, $C_1$-$C_2$ alkyl halide, $C_1$-$C_4$ alkylcarbonyl, $C_1$-$C_4$ alkylcarbonyloxy, halogen, nitro or cyano, and X has the above-mentioned meaning. The inventive method is characterized in that the transformation takes place in the presence of hydrogen chloride and of an inert solvent, and in that a catalyst selected from the group comprised of: iron, indium or halogenides, oxides or triflates thereof is added to the reaction mixture.

25 Claims, No Drawings

METHOD FOR PRODUCING 2-CHLOROMETHYLPHENYL ACETIC ACID DERIVATIVES

CROSS REFERENCE TO RELATED APPLICATION

This application is a 35 USC § 371 National Phase Entry Application from PCT/EP03/01160, filed Feb. 6, 2003, and designating the U.S.

The present invention relates to a process for preparing 2-(chloromethyl)phenylacetic acid derivatives of the formula I,

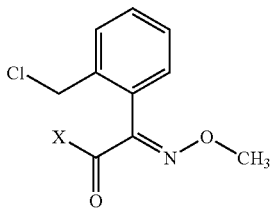

where X is $C_1$-$C_4$-alkoxy or methylamino, by ether cleavage of compounds of the formula II,

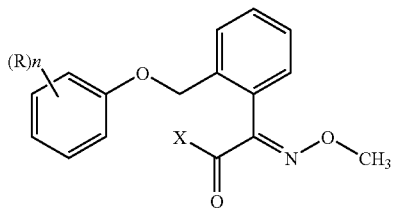

where R is $C_1$-$C_4$-alkyl, $C_1$-$C_4$-alkoxy, $C_1$-$C_2$-haloalkyl, $C_1$-$C_4$-alkylcarbonyl, $C_1$-$C_4$-alkylcarbonyloxy, halogen, nitro or cyano and X is as defined above.

J. Chem. Research (S) 232-3 (1985) and J. Org. Chem. 64, 4545 (1981) disclose methods for cleaving benzyl ethers in the presence of specific Lewis acids such as sodium iodide/boron trifluoride or iron(III) chloride on silica. The Lewis acids are used in greater than stoichiometric quantities, which makes the process uneconomical.

Synlett (10), 1575-6 (1999) describes a process for cleaving 4-nitrobenzyl ethers in the presence of indium and aqueous ammonium chloride. Indium is used in an excess of more than 8 equivalents based on the ether to be cleaved.

A process for preparing 2-(chloromethyl)phenyl acetic acid derivatives of the formula I by cleaving the appropriate benzyl ethers II is described in WO-A 97/21686. This involves admixing the benzyl ether II with an excess of two or more mol equivalents of boron trichloride.

The prior art processes use greater than stoichiometric quantities of Lewis acids. The handling of Lewis acids used is additionally problematic and the majority thereof are highly corrosive.

It is an object of the present invention to provide a catalytic process for preparing 2-(chloromethyl)phenylacetic acid derivatives of the formula I from the appropriate benzyl ethers in high yield and selectivity which does not have the above-mentioned disadvantages. Care also had to be taken that the benzyl ether II was cleaved with high selectivity, i.e. that the methoxyiminophenylglyoxylic acid unit in the target compound I was retained.

We have found that this object is achieved by carrying out the ether cleavage in the presence of hydrogen chloride and an inert solvent, and adding a catalyst to the reaction mixture selected from the group consisting of iron, indium and halides, oxides and triflates thereof.

The hydrogen chloride is generally passed into the reaction mixture in gaseous form. However, it is also possible to condense in the hydrogen chloride. In general, the hydrogen chloride is used in a molar ratio relative to the benzyl ether of from 1 to 25, preferably from 1 to 10 and more preferably from 3 to 5 mol equivalents.

Useful catalysts include Lewis acids selected from the group consisting of iron, indium and halides, oxides and triflates thereof. Preferred catalysts are iron and indium(III) chloride and also in particular iron(III) oxide and iron(III) chloride. The catalyst is used in a concentration of from 0.001 to 0.5 and preferably from 0.01 to 0.2 mol equivalents.

Useful solvents include aromatic (halogenated) hydrocarbons, e.g. benzene, toluene, xylene, chlorobenzene, dichlorobenzene, bromobenzene and benzotrifluoride; aliphatic (halogenated) hydrocarbons, e.g. pentane, heptane, dichloromethane, chloroform, 1,2-dichloroethane and carbon tetrachloride; cycloaliphatic hydrocarbons, e.g. cyclohexane and cyclopentane; ethers, e.g. dimethoxyethane, diethyl ether and di-isopropyl ether; and esters, e.g. ethyl acetate and butyl acetate. Mixtures of these solvents may also be used.

Preferred solvents are aromatic (halogenated) hydrocarbons and aliphatic (halogenated) hydrocarbons.

It may possibly be advantageous to add Lewis bases, e.g. pyridine, N,N-dimethylaniline or ethanethiol and/or further auxiliaries such as trimethylsilyl chloride, to the reaction mixture.

It may also be advantageous to work in a biphasic system in the presence of a phase transfer catalyst, e.g. tetrabutylammonium chloride, tetrahexylammonium chloride, tetrabutylphosphonium chloride, bis(triphenylphosphoranylidene) ammonium chloride, trimethylbenzylammonium chloride, triethylbenzylammonium chloride or triphenylbenzylammonium chloride.

The reaction temperature is customarily from 0 to 100° C. and preferably from 30 to 70° C. The reaction pressure is customarily from 0 to 6 bar. Preference is given to carrying out the reaction under atmospheric pressure.

It is also advantageous to perform the ether cleavage under a protective gas atmosphere.

Useful starting materials for the ether cleavage include the benzyl ethers II mentioned at the outset. They are accessible by literature methods (EP-A 253 213, EP-A 254 426, EP-A 398 692 or EP-A 477 631). In particular, the crop protection agents currently on the market are suitable, for example methyl 2-methoxyimino-2-[(2-methylphenyloxymethyl) phenyl] acetate (Kresoxim-methyl, EP-A 253 213).

After the ether cleavage, the reaction mixture is generally worked up by extraction. Catalyst impurities may be removed, for example, by extraction using aqueous mineral acid such as hydrochloric acid. The phenol cleavage product may advantageously be removed by extraction using aqueous alkali such as sodium hydroxide.

The 2-(chloromethyl)phenylacetic acid derivative obtained may be further processed directly, dissolved in the inert solvent, or as a melt after distillative removal of the solvent.

The crude product can be further purified by recrystallization in alcohols such as methanol, ethanol, n-butanol or mixtures thereof or mixtures of alcohols and dimethylformamide. The crude product can also be purified by melt crystallization.

PROCESS EXAMPLES

Inventive Example 1

7.5 g (24 mmol) of kresoxim-methyl were dissolved in 150 ml of chlorobenzene. 0.32 g (2.4 mmol) of iron(III) chloride were then added and 2.6 g (72 mmol) of hydrogen chloride were gassed in within 1 h, during the heating phase to 50° C. The reaction mixture was held at 50° C. for a further 2 hours with stirring and the conversion was then monitored by means of HPLC. After the reaction had ended, the reaction solution was cooled and admixed with 10 ml of methanol. The reaction mixture was extracted, first with hydrochloric acid and then with sodium hydroxide. The organic phase was washed to neutrality and then freed of solvent. The yield of methyl 2-methoxyimino-2-[(2-chloromethyl)phenyl]acetate was 75%.

Inventive Example 2

7.5 g (24 mmol) of kresoxim-methyl were dissolved in 150 ml of toluene. 0.53 g (2.4 mmol) of indium(III) chloride were then added and 2.6 g (72 mmol) of hydrogen chloride were gassed in within 1 h, during the heating phase to 40° C. The reaction mixture was held at 40° C. for a further 4 hours with stirring and then worked up as in inventive example 1. The yield of methyl 2-methoxyimino-2-[(2-chloromethyl)phenyl]acetate was 80%.

Inventive Example 3

The ether cleavage of inventive example 1 was repeated in 150 ml of 1,2-dichloroethane. 4.1 g (112 mmol) of hydrogen chloride were gassed in within 1 h, during the heating phase to 100° C., and the reaction mixture was held at 100° C. for a further 5 hours. The yield of product of value was 80%.

Comparative Example 4

7.5 g (24 mmol) of kresoxim-methyl were dissolved in 150 ml of toluene. 0.32 g (2.4 mmol) of aluminum chloride were then added and 2.6 g (72 mmol) of hydrogen chloride were gassed in within 1 h, during the heating phase to 100° C. The reaction mixture was held at 100° C. for a further 2 hours with stirring and then worked up as in inventive example 1. The yield of product of value was 30%.

Comparative Example 5

7.5 g (24 mmol) of kresoxim-methyl were dissolved in 150 ml of 1,2-dichloroethane. 0.63 g (2.4 mmol) of tin tetrachloride were then added and 2.6 g (72 mmol) of hydrogen chloride were gassed in within 1 h, during the heating phase to 85° C. The reaction mixture was held at 85° C. for a further 4 hours with stirring and then worked up as in Inventive Example 1. The yield of product of value was 30%.

We claim:

1. A process for preparing a 2-(chloromethyl)phenylacetic acid compound of formula I,

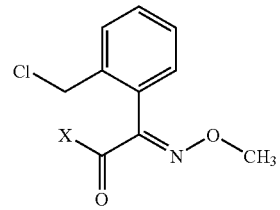

where X is C1-C4-alkoxy or methylamino, said process comprising cleaving by ether cleavage a compound of formula II,

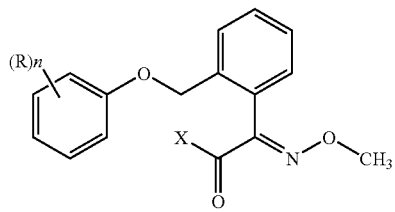

where R is C1-C4-alkyl, C1-C4-alkoxy, C1-C2-haloalkyl, C1-C4-alkylcarbonyl, C1-C4-alkylcarbonyloxy, halogen, nitro or cyano and X is as defined above, with hydrogen chloride, in the presence of an inert solvent and a catalyst, wherein said catalyst is selected from the group consisting of iron, iron halides, iron oxides, iron triflates, indium, indium halides, indium oxides and indium triflates.

2. The process of claim 1, wherein said catalyst is iron (III) chloride.

3. The process of claim 1, wherein said catalyst is iron.

4. The process of claim 1, wherein said catalyst is indium (III) chloride.

5. The process of claim 1, wherein said catalyst is iron (III) oxide.

6. The process of claim 1, wherein said catalyst has a concentration in the components of the ether cleaving reaction of about 0.001 to 0.5 mol equivalents.

7. The process of claim 1, wherein said catalyst has a concentration in the components of the ether cleaving reaction of about 0.01 to 0.2 mol equivalents.

8. The process of claim 1, wherein said hydrogen chloride has a concentration in the components of the ether cleaving reaction of about 1 to 25 mol equivalents.

9. The process of claim 1, wherein said hydrogen chloride has a concentration in the components of the ether cleaving reaction of about 1 to 10 mol equivalents.

10. The process of claim 1, wherein said hydrogen chloride has a concentration in the components of the ether cleaving reaction of about 3 to 5 mol equivalents.

11. The process of claim 1, wherein said inert solvent is an aromatic hydrocarbon.

12. The process of claim 1, wherein said inert solvent is an aliphatic (halogenated) hydrocarbon.

13. The process of claim 1 wherein said hydrogen chloride is passed into the ether cleaving reaction mixture in gaseous form.

14. The process of claim 1 wherein said hydrogen chloride is condensed into said ether cleaving reaction.

15. The process of claim 1 further comprising adding at least one Lewis base to the said ether cleaving reaction.

16. The process of claim 15 wherein said Lewis base is pyridine.

17. The process of claim 15 wherein said Lewis base is N,N-dimethylaniline.

18. The process of claim 15 wherein said Lewis base is ethanethiol.

19. The process of claim 1 further comprising adding trimethylsilyl chloride to said ether cleaving reaction.

20. The process of claim 1 further comprising conducting said ether cleaving reaction in a biphasic system in the presence of a phase transfer catalyst, wherein the phase transfer catalyst is selected from the group consisting of tetrabutylammonium chloride, tetrahexylammonium chloride, tetrabutylphosphonium chloride, bis(triphenylphosphoranylidene) ammonium chloride, trimethylbenzylammonium chloride, triethylbenzyammonium chloride and triphenylbenzylammonium chloride.

21. The process of claim 1 further comprising performing said ether cleaving reaction under a protective gas atmosphere.

22. The process of claim 1 wherein said ether cleaving reaction temperature is between about 0 to 100° C.

23. The process of claim 1 wherein said ether cleaving reaction temperature is between about 30 to 70° C.

24. The process of claim 1 wherein said ether cleaving reaction pressure is from about 0 to 6 bar.

25. The process of claim 1 wherein said ether cleaving reaction pressure is atmospheric pressure.

* * * * *